US010017795B2

(12) United States Patent
Chandran

(10) Patent No.: US 10,017,795 B2
(45) Date of Patent: Jul. 10, 2018

(54) METHODS AND SYSTEMS FOR CONVERTING VOLATILE FATTY ACIDS TO LIPIDS

(71) Applicant: The Trustees of Columbia University in the City of New York, New York, NY (US)

(72) Inventor: Kartik Chandran, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 311 days.

(21) Appl. No.: 14/567,271

(22) Filed: Dec. 11, 2014

(65) Prior Publication Data

US 2015/0167035 A1    Jun. 18, 2015

Related U.S. Application Data

(60) Provisional application No. 62/090,102, filed on Dec. 10, 2014, provisional application No. 61/915,788, filed on Dec. 13, 2013.

(51) Int. Cl.
*C12P 7/64* (2006.01)
*C12P 5/02* (2006.01)
*C12M 1/107* (2006.01)
*C12M 1/00* (2006.01)

(52) U.S. Cl.
CPC ........... *C12P 7/6409* (2013.01); *C12M 21/04* (2013.01); *C12M 23/58* (2013.01); *C12P 5/023* (2013.01); *C12P 7/6445* (2013.01); *Y02E 50/13* (2013.01); *Y02E 50/343* (2013.01)

(58) Field of Classification Search
None
See application file for complete search history.

(56) References Cited

U.S. PATENT DOCUMENTS

| 2012/0219993 | A1* | 8/2012 | Chang | C12P 21/00 435/71.1 |
| 2014/0027373 | A1* | 1/2014 | Josse | C02F 3/282 210/605 |

FOREIGN PATENT DOCUMENTS

EP    2130618    *    9/2009

OTHER PUBLICATIONS

Ahring et al. "Volatile fatty acids as indicators of process imbalance in anaerobic digestors" Appl Microbiol Biotechnol (1995) 43:559-565.*
Labatut et al. "Monitoring of Anaerobic Digestion Process to Optimize Performance and Prevent System Failure" excerpt taken from Got Manure? Enhancing Environmental and Economic Sustainability Conference, Mar. 28-29, 2012, 25 pages.*
Wang et al. "Evaluation of a Novel Split-Feeding Anaerobic/Oxic Baffled Reactor (A/OBR) for Foodwaste Anaerobic Digestate: Performance, Modeling" Scientific Reports | 6:34640 | DOI: 10.1038/srep34640, 14 pgs (Year: 2016).*

* cited by examiner

*Primary Examiner* — Thane Underdahl
(74) *Attorney, Agent, or Firm* — Murtha Cullina LLP; Anthony P. Gangemi

(57) ABSTRACT

Methods and systems for simultaneously enhancing the production of both methane and volatile fatty acids in an anaerobic digestion bioreactor are disclosed. In some embodiments, the methods include: providing a stream of organic feedstock; providing a plurality of anaerobic digester bioreactors, each of the plurality of anaerobic digester bioreactors connected in series; step-feeding predetermined percentages of the stream of organic feedstock to two or more of the plurality of anaerobic digester bioreactors; feeding effluent from each of the plurality of anaerobic digester bioreactors to a subsequent one of the plurality of anaerobic digester bioreactors; and anaerobically digesting at least one of the stream of organic feedstock and the effluent from each of the plurality of anaerobic digester bioreactors to develop a final effluent stream including methane and volatile fatty acids. The volatile fatty acids are then microbially converted to lipids in an aerobic bioreactor.

13 Claims, 2 Drawing Sheets

METHODS AND SYSTEMS FOR CONVERTING VOLATILE FATTY ACIDS TO LIPIDS

CROSS REFERENCE TO RELATED APPLICATION(S)

This application claims the benefit of U.S. Provisional Application Nos. 61/915,788, filed Dec. 13, 2013 and 62/090,102, filed Dec. 10, 2014, each of which is incorporated by reference as if disclosed herein in its entirety.

BACKGROUND

In developing countries, 2.6 billion people remain without access to any kind of sanitation and 850 million remain undernourished. Thus, there is a critical need to develop sustainable technologies that provide sanitation while simultaneously recovering valuable nutrients and resources from the waste. Biofuels have not found widespread application so far because of higher cost and the significant stress they exert upon the agricultural commodities.

Biocatalysis of organic waste into useful chemical feedstock is a promising approach for managing waste and providing a renewable energy supply such as diesel. However, many current methods for producing renewable energy sources suffer from low yields and/or production from food commodities resulting in competition for crop resources.

Most lipids for commercial biodiesel production today are derived from food and agricultural commodities, e.g. soybean, jatropha oil, etc., inadvertently contributing to the rising food prices. Therefore, it is preferred to produce non-edible sources of lipids, in particular, lipids derived from oleaginous microorganisms such as yeast and other fungi, which have the capability to assimilate inexpensive organic carbon sources produced from existing technologies such as anaerobic fermentation and digestion and store them as lipids.

Anaerobic digestion has been practiced for centuries, but is still plagued by limitations to adequate mixing in the anaerobic bioreactors. Additionally, using bioreactor designs and operating configurations developed to date, it is only possible to either maximize methane production or volatile fatty acids. This results in high operating and capital costs for a given methane or acid output.

Organic material from waste water, sewage, and industrial waste can be reused to produce biogas using anaerobic digestion. Biogas, such as methane and volatile fatty acids, can be used for energy and as building blocks for chemical production, respectively. In anaerobic digestion, the organic material, or feedstock, is dissolved in water and mixed with methane and acid producing bacteria. However, current anaerobic digestion bioreactors suffer from lower yields of biogas production due to limited mixing between the feedstock and bacteria. In addition, the design of these bioreactors also allows for maximizing the yields of either methane or volatile fatty acids only, but not both.

SUMMARY

Methods and systems according to the disclosed subject matter include anaerobic bioreactors using a step feed pattern to simultaneously increase the yield of methane and volatile fatty acid production. A step feed pattern introduces the feedstock to the bioreactor during different stages of digestion, rather than all the material at once in the beginning. This step feed pattern allows better mixing of the feedstock with the microbes, increasing the yield and kinetics of both methane and volatile fatty acid production in computer simulations. In addition, the step feed design allows the bioreactor to consist of multiple smaller tanks that may be better suited for environments with less available space.

Some embodiments of the disclosed subject matter include an aerobic biological process, wherein the volatile fatty acids produced from anaerobic fermentation of various substrates, are converted into lipids. In some embodiments, the biocatalysts used include yeast and fungi, which are cultivated in aerated reactors and fed with volatile fatty acids. By optimizing process operating conditions including pH, hydraulic retention time, initial or influent volatile fatty acid concentration and the relative organic carbon to nitrogen ratio in the feed, the lipid content of the biocatalysts is maximized.

Some embodiments of the disclosed subject matter include a method to produce lipids using substrates, i.e., volatile fatty acids, which are widely produced during anaerobic digestion of organic wastes and substrates. Lipids are an attractive product, since they can be converted directly to biodiesel. It is possible to convert just about any organic compound (through first anaerobic conversion to volatile fatty acids) to lipids. Systems according the disclosed subject matter are superior to current lipid pipelines for biodiesel, including algae, since the yeasts and fungi used herein can convert volatile fatty acids to lipids, which algae cannot.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Referring again to FIGS. 1 and 2, aspects of the disclosed subject matter include methods and systems using bioreactors for enhancing the production of both methane and volatile fatty acids and converting the volatile fatty acids to lipids.

Figure 1:
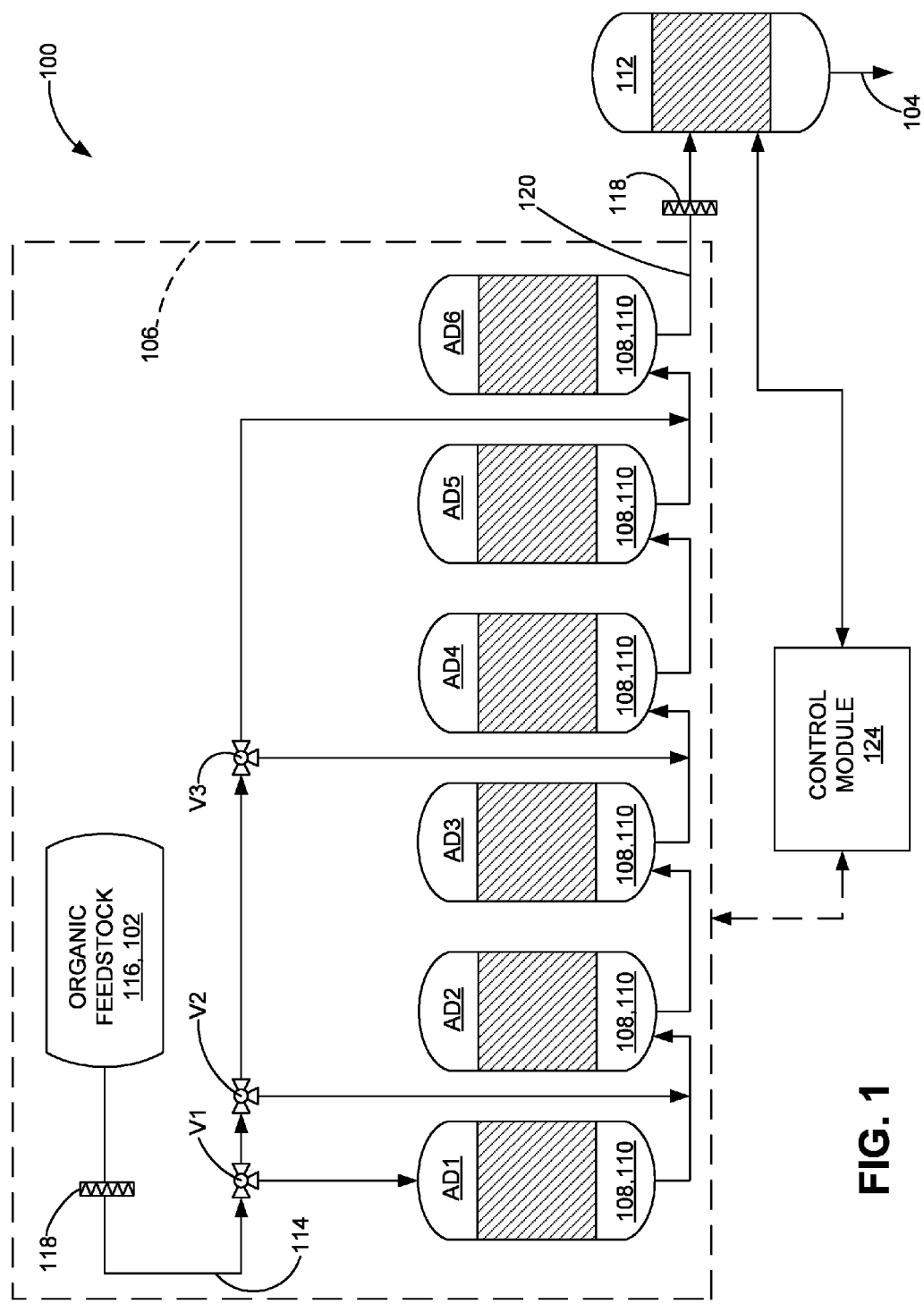
FIG. 1 is a schematic diagram of methods and systems according to some embodiments of the disclosed subject matter.

Referring now to FIG. 1, some embodiments include a system 100 for converting volatile fatty acids 102 to lipids 104 using a feedstock treatment module 106 to produce both methane 108 and volatile fatty acids 110 and an aerobic bioreactor 112 for converting the volatile fatty acids to lipids.

System 100 includes a supply stream of organic feedstock 114 that is typically stored in a tank 116 and pumped to feedstock treatment module 106. Methods and systems according to the disclosed subject matter are adaptable for simultaneously enhancing the production of methane and volatile fatty acids from virtually any organic feedstock, including but not limited to the following: Wastewater; Sewage sludge; Fecal sludge; Agricultural waste; Animal processing waste; Municipal solid organic waste; Food waste; and Industrial waste, including but not limited to brewery waste, pharmaceutical waste, biodiesel waste, chemical waste.

Feedstock treatment module 106 is used to enhance the production of both methane and volatile fatty acids from supply stream of organic feedstock 114. Feedstock treatment module 106 includes a plurality of anaerobic digester bioreactors, e.g., in some embodiments as shown in FIG. 1, there are six bioreactors, AD1-AD6, that are fluidly connected in series and fluidly joined with supply stream of organic feedstock 114. A plurality of adjustable diverter valves (V1-V3) are used for step-feeding predetermined percentages of supply stream of organic feedstock 114 to two or more, e.g., in some embodiments, as shown in FIG. 1, four bioreactors, AD1, AD2, AD4, and AD6, of plurality of anaerobic digester bioreactors (AD1-AD6). In some, but not all embodiments, system 100 includes a feedstock pretreatment filter 118 for sterilizing volatile fatty acids 102 included in supply stream of organic feedstock 114 before they are fed to plurality of anaerobic digester bioreactors (AD1-AD6). In some embodiments, e.g., where feedstock 114 is pre-fermented with high concentrations of volatile fatty acids, feedstock pretreatment filter 118 is placed after the final bioreactor, i.e., AD6 in FIG. 1, and the volatile fatty acids are sterilized prior to feeding them to aerobic bioreactor 112. After supply stream of organic feedstock 114 passes through anaerobic digester bioreactors AD1-AD6, a final effluent stream 120, which includes enhanced amounts of methane 108 and volatile fatty acids 110, exits the last one of the bioreactors in the series, i.e., AD6 in FIG. 2. In some embodiments, a substantial amount of the methane present and produced is collected from one or more of anaerobic digester bioreactors AD1-AD6 and only a nominal amount of methane 108 is present in final effluent stream 120.

In some embodiments, one of the plurality of anaerobic digester bioreactors, e.g., AD1, is step-fed about 50 to about 80 percent of supply stream of organic feedstock 114 and three of the plurality of anaerobic digester bioreactors, e.g., AD2, AD4, and AD6, are each step-fed about 5 to about 15 percent of the supply stream of organic feedstock. In some embodiments, one of the plurality of anaerobic digester bioreactors, e.g., AD1, is step-fed about 70 percent of supply stream of organic feedstock 114 and three of the plurality of anaerobic digester bioreactors, e.g., AD2, AD4, and AD6, are each step-fed about 10 percent of the supply stream of organic feedstock. As one skilled in the art will appreciate, the particular flow split percentages of supply stream of organic feedstock 114 that are sent to particular ones of the bioreactors varies depending on the characteristics of the feedstock.

In some embodiments, final effluent stream 120 exits feedstock treatment module 106 and enters aerobic bioreactor 112 where volatile fatty acids 110 are microbially converted to lipids 104. Typically, but not always, microorganisms including *Cryptococcus albidus* yeast or *Fusarium oxysporum* fungus microbially converts volatile fatty acids in final effluent stream 120 to lipids 104.

In some embodiments, control module 124 includes a plurality of monitors (not shown), e.g., wired or wireless, and a plurality of remotely actuated valves (also not shown), which automatically monitor and adjust operating conditions in plurality of anaerobic digester bioreactors (AD1-AD6) and aerobic bioreactor 112 by controlling diverter valves V1-V3 and other valves not shown, by controlling one or more pumps (not shown) to adjust the flow, by controlling appropriate equipment (also not shown) to adjust temperatures in the bioreactors, by causing nitrogen or compounds including nitrogen to be added to one or more of the bioreactors to adjust the initial nitrogen concentration in aerobic bioreactor 112, and causing acidic or basic chemicals to be added to the bioreactors to adjust the pH. For example, in some embodiments, the temperature in each of the plurality of anaerobic digester bioreactors is maintained at about 20 to about 40 degrees Celsius, the pH in each of the plurality of anaerobic digester bioreactors is maintained at about 5.5 to about 7.0, and an initial nitrogen concentration in final effluent stream 120 is about 4 to about 10 percent of an initial volatile fatty acid concentration 102 in supply stream of organic feedstock 114.

Figure 2:
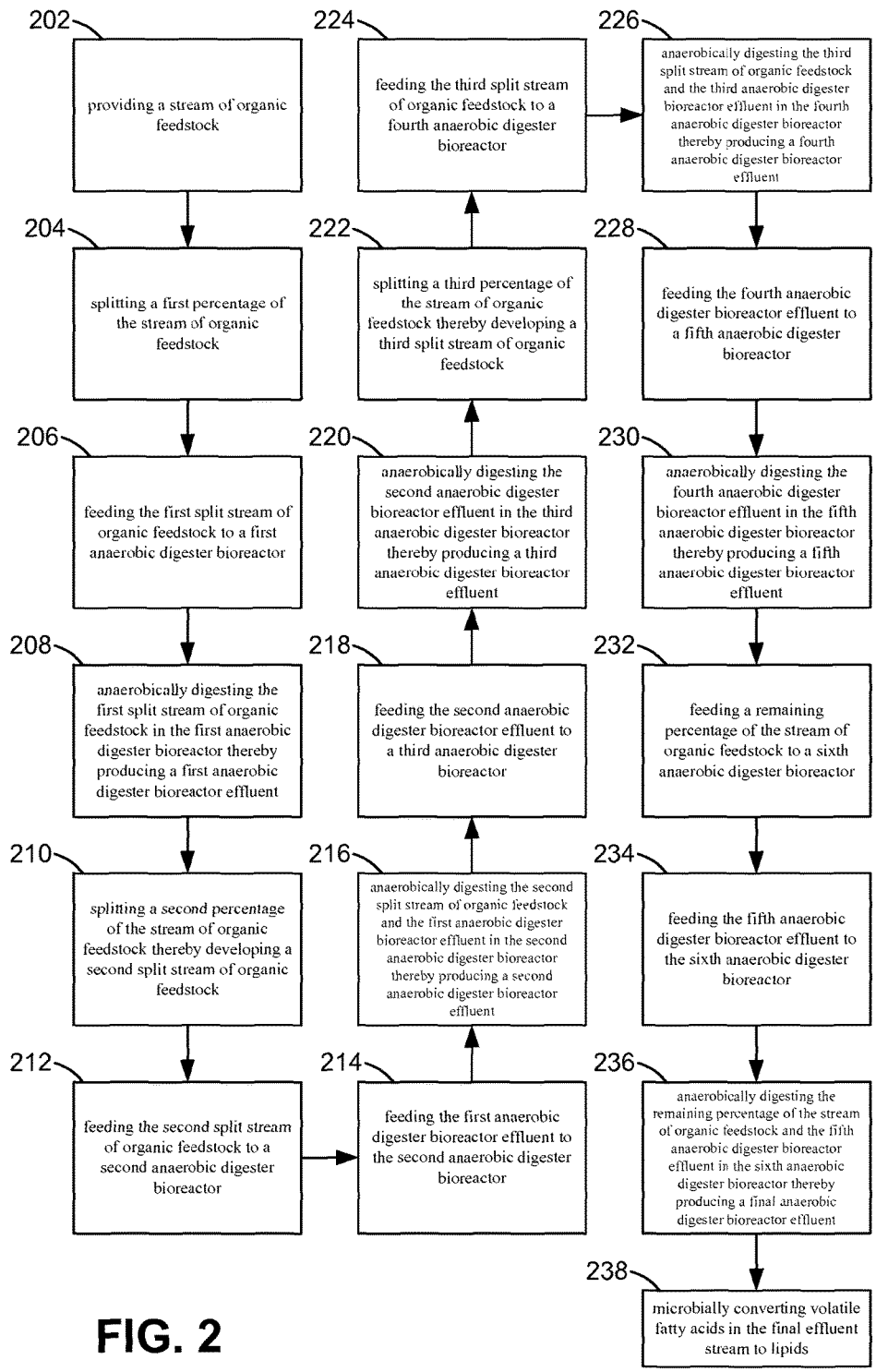
FIG. 2 is a chart of a method according to some embodiments of the disclosed subject matter.

Referring now to FIG. 2, some embodiments include a method 200 for simultaneously enhancing the production of both methane and volatile fatty acids in an anaerobic digestion bioreactor. At 202, a stream of organic feedstock is provided. At 204, a first percentage of the stream of organic feedstock is split from the stream thereby developing a first split stream of organic feedstock. In some embodiments, the first percentage is about 50 to about 80 percent of the stream of organic feedstock. In some embodiments, the first percentage is about 70 percent of the stream of organic feedstock. At 206, the first split stream of organic feedstock is fed to a first anaerobic digester bioreactor. At 208, the first split stream of organic feedstock is anaerobically digested in the first anaerobic digester bioreactor thereby producing a first anaerobic digester bioreactor effluent including methane and volatile fatty acids. At 210, a second percentage of the stream of organic feedstock is split from the stream thereby developing a second split stream of organic feedstock. In some embodiments, the second percentage is about 5 to about 15 percent of the stream of organic feedstock. In some embodiments, the second percentage is about 10 percent of the stream of organic feedstock. At 212, the second split stream of organic feedstock is fed to a second anaerobic digester bioreactor. At 214, the first anaerobic digester bioreactor effluent is fed to the second anaerobic digester bioreactor. At 216, the second split stream of organic feedstock and the first anaerobic digester bioreactor effluent are anaerobically digested in the second anaerobic digester bioreactor thereby producing a second anaerobic digester bioreactor effluent including methane and volatile fatty acids. At 218, the second anaerobic digester bioreactor effluent is fed to a third anaerobic digester bioreactor. At 220, the second anaerobic digester bioreactor effluent is anaerobically digested in the third anaerobic digester bioreactor thereby producing a third anaerobic digester bioreactor effluent including methane and volatile fatty acids. At 222, a third percentage of the stream of organic feedstock is split from the stream thereby developing a third split stream of organic feedstock. In some embodiments, the third percentage is about 5 to about 15 percent of the stream of organic feedstock. In some embodiments, the third percentage is about 10 percent of the stream of organic feedstock. At 224, the third split stream of organic feedstock is fed to a fourth anaerobic digester bioreactor. At 226, the third split stream of organic feedstock and the third anaerobic digester bioreactor effluent are anaerobically digested in the fourth anaerobic digester bioreactor thereby producing a fourth anaerobic digester bioreactor effluent including methane and volatile fatty acids. At 228, the fourth anaerobic digester bioreactor effluent is fed to a fifth anaerobic digester bioreactor. At 230, the fourth anaerobic digester bioreactor effluent is anaerobically digested in the fifth anaerobic digester bioreactor thereby producing a fifth anaerobic digester bioreactor effluent including methane and volatile fatty acids. At 232, a remaining percentage of the stream of organic feedstock is fed to a sixth anaerobic digester bioreactor. In some embodiments, the remaining percentage is about 5 to about 15 percent of the stream of organic feedstock. In some embodiments, the remaining percentage is about 10 percent of the stream of organic feedstock. At 234, the fifth anaerobic digester bioreactor effluent is fed to the sixth anaerobic digester bioreactor. At 236, the remaining percentage of the stream of organic feedstock and the fifth anaerobic digester bioreactor effluent are anaerobically digested in the sixth anaerobic digester bioreactor thereby producing a final anaerobic digester bioreactor effluent including methane and volatile fatty acids. At 238, the final anaerobic digester bioreactor effluent is fed to an aerobic bioreactor and the volatile fatty acids are microbially converted to lipids.

Methods and systems according to the disclosed subject matter provide a distinct commercial and technological advantage overall existing anaerobic bioreactor designs in that it maximizes the production of both methane and volatile fatty acids by employing a novel step-feed strategy. The step-feed strategy additional provides enhanced mixing of the feedstock in the bioreactor, thereby increasing process kinetics and efficiency even further, without the need for cost and energy intensive external mixing devices. Methods and systems according to the disclosed subject matter are adaptable for simultaneously enhancing the production of methane and volatile fatty acids from virtually any organic feedstock.

Methods and systems according to the disclosed subject matter employ specific step-feeding conditions for the anaerobic digestion process, which simultaneously maximize methane and volatile fatty acid yields and in addition enhance reactor mixing. Step-feeding to anaerobic digesters is unique.

The main advantages of methods and systems according to the disclosed subject matter are as follows: 1. Simultaneous maximization of methane and volatile fatty acid concentrations; and 2. Enhanced anaerobic reactor mixing.

Methods and systems according to the disclosed subject matter are adaptable for simultaneously enhancing the production of methane and volatile fatty acids from virtually any organic feedstock and can also be applied to waste streams from existing domestic (including, but not limited to high-rise multi-dwelling communities, new residential or commercial developments, hospital or educational complexes).

Methods and systems according to the disclosed subject matter are a novel way to produce lipids using substrates (volatile fatty acids), which are widely produced during anaerobic digestion of organic wastes and substrates. Using methods and systems according to the disclosed subject, it is possible to convert the volatile fatty acids into lipids. Lipids are an attractive product, since they can be converted directly to biodiesel. Therefore, it is possible to convert just about any organic compound (through first anaerobic conversion to volatile fatty acids) to lipids. This system is also superior to current lipid pipelines for biodiesel, including algae, since the yeasts and fungi used herein can convert volatile fatty acids to lipids, which algae cannot. Additionally, this technology avoids the use of food commodities for the production of biodiesel, including from jatropha or cooking oils. Instead, it provides a flexible platform for integrating waste treatment into biofuels (biodiesel) production.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A method for simultaneously enhancing the production of both methane and volatile fatty acids in an anaerobic digestion bioreactor, said method comprising:
   providing a stream of organic feedstock;
   providing a plurality of anaerobic digester bioreactors, each of said plurality of anaerobic digester bioreactors connected in series;
   step-feeding predetermined percentages of said stream of organic feedstock to two or more of said plurality of anaerobic digester bioreactors connected in series;
   feeding effluent from each of said plurality of anaerobic digester bioreactors to a subsequent one of said plurality of anaerobic digester bioreactors in said connected series of anaerobic digester bioreactors; and
   anaerobically digesting at least one of said stream of organic feedstock and said effluent from each of said plurality of anaerobic digester bioreactors to develop a final effluent stream including methane and volatile fatty acids;
   wherein at least one of said plurality of anaerobic digester bioreactors is fed about 50 to about 80 percent of said stream of organic feedstock and at least two of said plurality of anaerobic digester bioreactors are each fed about 5 to about 15 percent of said stream of organic feedstock.

2. The method according to claim 1, wherein said plurality of anaerobic digester bioreactors includes six bioreactors.

3. The method according to claim 1, wherein one of said plurality of anaerobic digester bioreactors is fed about 70 percent of said stream of organic feedstock and three of said plurality of anaerobic digester bioreactors are each fed about 10 percent of said stream of organic feedstock.

4. The method according to claim 1, wherein said organic feedstock includes one or more of wastewater, sewage sludge, fecal sludge, agricultural waste, animal processing waste, municipal solid organic waste, food waste, and industrial waste.

5. The method according to claim 1, wherein an initial nitrogen concentration in said final effluent stream is about 4 to about 10 percent of an initial volatile fatty acid concentration in said stream of organic feedstock.

6. The method according to claim 1, wherein a temperature in each of said plurality of anaerobic digester bioreactors is maintained at about 20 to about 40 degrees Celsius.

7. The method according to claim 1, wherein a pH in each of said plurality of anaerobic digester bioreactors is maintained at about 5.5 to about 7.0.

8. The method according to claim 1, further comprising sterilizing volatile fatty acids in said final effluent stream to an aerobic reactor using a 0.2 µm filter.

9. The method according to claim 1, further comprising:
   microbially converting volatile fatty acids in said final effluent stream to lipids.

10. The method according to claim 9, wherein organisms including a *Cryptococcus albidus* yeast, a *Fusarium oxysporum* fungus, or a combination thereof, microbially convert volatile fatty acids in said final effluent stream to lipids.

11. A method for simultaneously enhancing the production of both methane and volatile fatty acids in an anaerobic digestion bioreactor, said method comprising:
    providing a stream of organic feedstock;

splitting a first percentage from said stream of organic feedstock thereby developing a first split stream of organic feedstock;

feeding said first split stream of organic feedstock to a first anaerobic digester bioreactor;

anaerobically digesting said first split stream of organic feedstock in said first anaerobic digester bioreactor thereby producing a first anaerobic digester bioreactor effluent including methane and volatile fatty acids;

splitting a second percentage from said stream of organic feedstock thereby developing a second split stream of organic feedstock;

feeding said second split stream of organic feedstock to a second anaerobic digester bioreactor;

feeding said first anaerobic digester bioreactor effluent to said second anaerobic digester bioreactor;

anaerobically digesting said second split stream of organic feedstock and said first anaerobic digester bioreactor effluent in said second anaerobic digester bioreactor thereby producing a second anaerobic digester bioreactor effluent including methane and volatile fatty acids;

feeding said second anaerobic digester bioreactor effluent to a third anaerobic digester bioreactor;

anaerobically digesting said second anaerobic digester bioreactor effluent in said third anaerobic digester bioreactor thereby producing a third anaerobic digester bioreactor effluent including methane and volatile fatty acids;

splitting a third percentage from said stream of organic feedstock thereby developing a third split stream of organic feedstock;

feeding said third split stream of organic feedstock to a fourth anaerobic digester bioreactor;

anaerobically digesting said third split stream of organic feedstock and said third anaerobic digester bioreactor effluent in said fourth anaerobic digester bioreactor thereby producing a fourth anaerobic digester bioreactor effluent including methane and volatile fatty acids;

feeding said fourth anaerobic digester bioreactor effluent to a fifth anaerobic digester bioreactor;

anaerobically digesting said fourth anaerobic digester bioreactor effluent in said fifth anaerobic digester bioreactor thereby producing a fifth anaerobic digester bioreactor effluent including methane and volatile fatty acids;

feeding a remaining percentage of said stream of organic feedstock to a sixth anaerobic digester bioreactor;

feeding said fifth anaerobic digester bioreactor effluent to said sixth anaerobic digester bioreactor; and anaerobically digesting said remaining percentage of said stream of organic feedstock and said fifth anaerobic digester bioreactor effluent in said sixth anaerobic digester bioreactor thereby producing a final anaerobic digester bioreactor effluent including methane and volatile fatty acids.

12. The method according to claim 11, wherein said first percentage is about 50 to about 80 and said second, third, and remaining percentages are each about 5 to about 15.

13. The method according to claim 11, wherein said first percentage is about 70 and said second, third, and remaining percentages are each about 10.

* * * * *